US012310622B2

(12) United States Patent
Bratlie

(10) Patent No.: US 12,310,622 B2
(45) Date of Patent: May 27, 2025

(54) IMPLANT REMOVAL METHOD

(71) Applicant: REMOVAID AS, Oslo (NO)

(72) Inventor: Marte Bratlie, Oslo (NO)

(73) Assignee: REMOVAID AS, Oslo (NO)

( * ) Notice: Subject to any disclaimer, the term of this patent is extended or adjusted under 35 U.S.C. 154(b) by 320 days.

(21) Appl. No.: 17/794,046

(22) PCT Filed: Jan. 20, 2021

(86) PCT No.: PCT/EP2021/051218
§ 371 (c)(1),
(2) Date: Jul. 20, 2022

(87) PCT Pub. No.: WO2021/148478
PCT Pub. Date: Jul. 29, 2021

(65) Prior Publication Data
US 2023/0090838 A1 Mar. 23, 2023

(30) Foreign Application Priority Data

Jan. 20, 2020 (GB) .................................. 2000807

(51) Int. Cl.
A61B 17/34 (2006.01)
A61B 17/3211 (2006.01)

(52) U.S. Cl.
CPC ...... A61B 17/3468 (2013.01); A61B 17/3211 (2013.01)

(58) Field of Classification Search
CPC ............ A61B 17/3468; A61B 17/3211; A61B 2017/00353; A61B 2017/320064; A61B 17/30; A61B 17/32093; A61B 17/50; A61B 17/285
See application file for complete search history.

(56) References Cited

U.S. PATENT DOCUMENTS

| 2014/0058409 | A1* | 2/2014 | Bratlie | ................... A61B 17/30 606/131 |
| 2016/0354115 | A1* | 12/2016 | Smith | ................ A61B 17/3468 |
| 2018/0168673 | A1* | 6/2018 | Bratlie | ................... A61B 17/50 |
| 2021/0322056 | A1* | 10/2021 | Moore | ............... A61B 17/3468 |

FOREIGN PATENT DOCUMENTS

| WO | 2013156628 A1 | 10/2013 |
| WO | 2016198381 A1 | 12/2016 |

OTHER PUBLICATIONS

Allergy and Anaesthesia: managing the risk—L. Savic (Year: 2020).*
Difficult removal of subdermal contraceptive implants: a multidisciplinary approach involving a peripheral nerve expert—Odom (Year: 2017).*
Chapter 4 Appendix 6: Standard implant removal—USAID Maternal and Child Survival Program (Year: 2017).*
(Continued)

Primary Examiner — Mohamed G Gabr
Assistant Examiner — Aman Kumar Mann
(74) Attorney, Agent, or Firm — Tarolli, Sundheim, Covell & Tummino LLP

(57) ABSTRACT

The present invention relates to a method for selecting a patient for an implant removal procedure, wherein the patient as a subcutaneously implanted rod and is in need of removal of said rod.

17 Claims, 3 Drawing Sheets

"PINCHABLE"

"NOT PINCHABLE"

(56) References Cited

OTHER PUBLICATIONS

Upstream Implant Removal Video (Pop-Out Method)—Innovating Education in Reproductive Health (Year: 2020).*

Internet Archive Screenshot for Upstream Implant Removal Video (Pop-Out Method) (Year: 2020).*

International Search Report and Written Opinion mailed May 11, 2021 for corresponding International Application No. PCT/EP2021/051218.

Lefebvre, R. et al. (2018). "Peripheral nerve injury with Nexplanon removal: case report and review of the literature" Contraception and Reproductive Medicine, 3(15). https://doi.org/10.1186/s40834-018-0070-0.

* cited by examiner

IMPLANT REMOVAL METHOD

RELATED APPLICATIONS

The present application is a U.S. National Stage application under 35 USC 371 of PCT Application Serial No. PCT/EP2021/051218, filed on 20 Jan. 2021; which claims priority from GB Patent Application No. 2000807.4, filed 20 Jan. 2020, the entirety of each of which are incorporated herein by reference.

FIELD OF THE INVENTION

The present invention relates to procedures associated with the removal of implanted rods, in particular contraceptive implant rods.

BACKGROUND OF THE INVENTION

Contraceptive Implants (CIs) were introduced to the commercial market in the early 1980s. They are advocated as a safe and effective method of contraception, and are included on the WHO's Essential Medicines list.

CI manufacturers have focused intense efforts on making insertion of CIs easier, but have largely left CI removals untouched and at the mercy of the various service providers. Different introducers and trocars are available for use with the different CI systems available internationally, and a second generation, single-use trocar is supplied with the Nexplanon® implant system available in Europe and the US. This second generation trocar has reduced the number of misplaced or deeply inserted CIs, and underlines the benefits of standardizing minor surgical procedures through the use of dedicated medical devices.

The CI removal procedure recommendations have been improved over the recent years, including the introduction of complex screening criteria (VAP score) to determine which implants may be suitable for removal by less experienced health care personnel. In health care, this is called "task sharing" and/or "Task Shifting", which is used describe a situation where a task normally performed by a cadre of health care staff is shared or transferred to a health professional with a different or lower level of education and training, or to a person specifically trained to perform a limited task only, without having a formal health education. Task shifting is common both in countries facing shortages of high-level health care staff and those not facing shortages.

The only currently described screening method in relation to implant removal is the Visibility Arrangement Palpability (VAP) scoring method. This is mainly used in scientific settings and may not be easily performed and/or interpreted by lower level health care staff as it requires the provider to categorize the implant by several subjective features that provides a numerical score to estimate potential difficulty of removal. Additionally, it is still somewhat subjective and cumbersome.

The method for removal has remained essentially unchanged for 40 years, relying on scalpels, forceps and general surgical skills from the service provider. Currently, no standardized technique for removal of CIs exists, and no dedicated CI removal device is found on the commercial market.

Removal of palpable subdermal implants is generally a simple, minor surgical office procedure. However, the procedure for implant removal requires more training and skill than the procedure for insertion. There is a risk of slippage of the scalpel blade or a sudden movement by the client causing inadvertent deeper penetration, in which case any underlying structure could be affected.

Mean removal times, from time of incision until removal of the rod, are consistently reported as less than 4 min, however with ranges from 0.2-60 min. Available research shows that the procedure length of the current CI removal procedure is highly variable and reliant on individual operator skills.

The RemovAid™ Retrieval Device is a single use surgically invasive Class IIa device intended for removal of CIs, which are small hormone-releasing plastic rods inserted under the skin, typically in the upper arm. A version of the device was described in WO2016/198381. RemovAid™ is intended to simplify and standardise the removal procedure to match the level of complexity to that of implant insertion and to reduce inter- and intra-operator procedural variability for implant removal. The intended time performance of the device is superior or at least equal to the current, standard implant removal procedure (i.e. manual removal with scalpels and forceps). Overall, the RemovAid™ combines the features of fixation, incision and extraction.

SUMMARY OF THE INVENTION

The present invention is based, at least in part, on the results of a clinical trial described herein (REVALID 02), which reported that the likelihood of successful removal of contraceptive implants with the RemovAid™ device is improved if certain conditions are fulfilled before attempting removal with the device. It was realised that those conditions could therefore form a screening test for determining whether or not a subcutaneous implanted rod can be removed with the RemovAid™ device. This test, as defined in the claims, may be referred to herein as the 'pinchability test'.

These 'pinchability test' applies not only to the RemovAid™ device, but would apply to any automatic removal device, i.e. any device that can be applied to the skin to fix the position of an implanted rod, and then optionally remove the rod through the skin.

Additionally, the 'pinchability test' of the invention may be used to determine a subset of subcutaneously implanted rods, for example contraceptive rods, which may be suitable for "task shifting", i.e. which may be suitable for removal by a less qualified healthcare practitioner, as "pinchable" implants are more superficially placed in the subdermis and not fastened to any underlying structure. Hence, the pinchability test may predict which implant removals are likely to be successfully performed by lower level health care personnel, with lower risk of adverse events such as nerve or vessel damage.

It is believed that the 'pinchability test' is a more effective method than the more complex VAP scoring system for contraceptive implants. The 'pinchability test' may be simpler to introduce into the clinical environment partly because the results are more easily interpreted by all levels of clinical staff.

The VAP score is loosely based on palpability, whereas the 'pinchability test' is based on being able to lift the implant away from the underlying layers of skin, i.e. being mobile under the skin. Without wishing to be bound by theory, if an implant is merely palpable, it may still be attached to the underlying skin structures by either fibrotic or adipocytic tissue. It may also be implanted too far into the skin, i.e. into the deeper layers of skin or even deeper structures such as muscles or tendons. This may cause the dissection/removal of the implant to be more difficult. However, if the implant is "pinchable", i.e. palpable and mobile relative to the underlying skin, this indicates that the removal of the implant will be simpler.

Therefore, according to a first aspect, the present invention is a method for selecting a patient for an implant removal procedure, wherein the patient has a subcutaneously implanted rod and is in need of removal of said rod, wherein the patient is selected as being suitable for the removal procedure if the rod can be gripped between a person's thumb and finger and the grip can be maintained while the person gently lifts the implant away from the underlying tissue.

According to a second aspect, the present invention is a method for removing a subcutaneously implanted rod from a patient in a removal procedure that comprises making an incision in the patient's skin and locating and removing the implanted rod through the opening in the skin, wherein the patient is selected for the removal procedure using the method as described herein.

According to a third aspect, the present invention is a kit comprising a medical device and instructions for use for the medical device, wherein the instructions for use comprise a description of the method as described herein.

DETAILED DESCRIPTION OF THE INVENTION

The screening/selection method of the invention is described above. The step of selecting a patient as being suitable for the removal procedure if the rod can be gripped between a person's thumb and finger and the grip can be maintained while the person gently lifts the implant away from the underlying tissue, may be referred to herein as the 'pinchability test'

Figure 2:
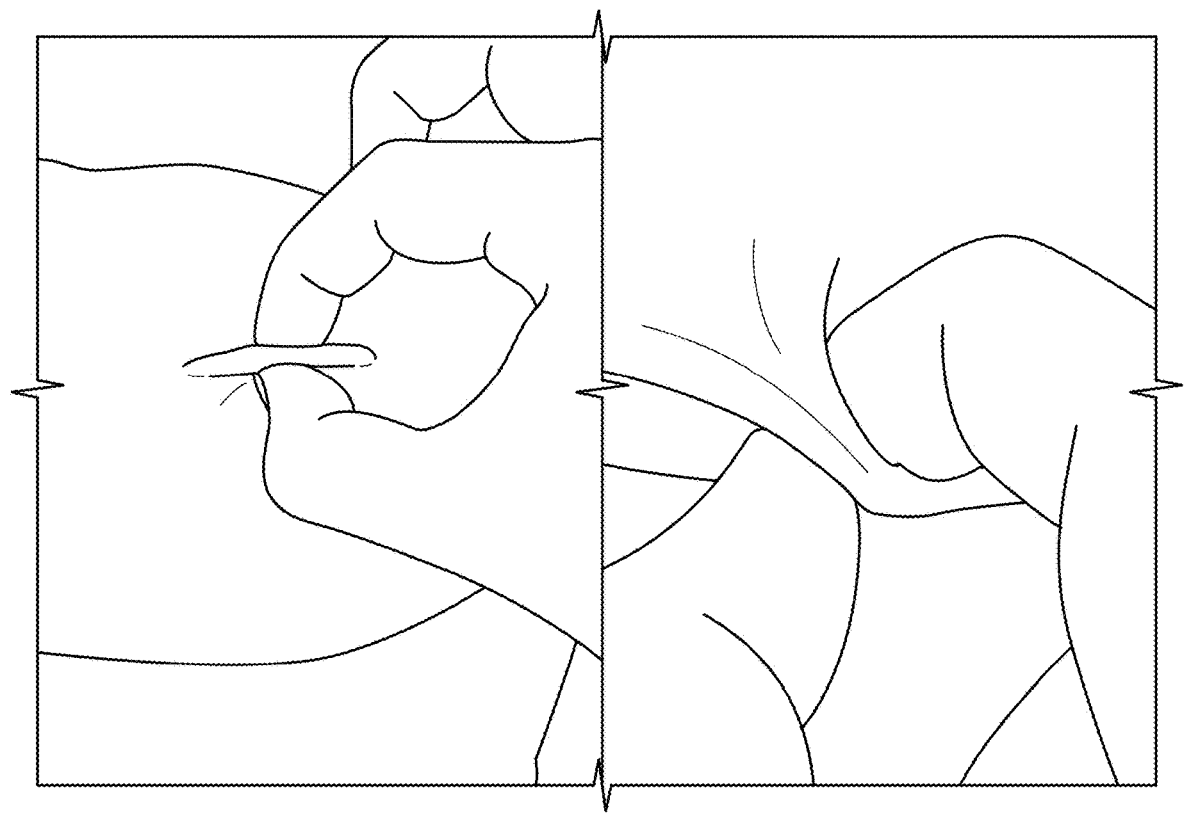
FIG. 2 shows an operator performing a 'pinchability' test of the invention.
Figure 3:
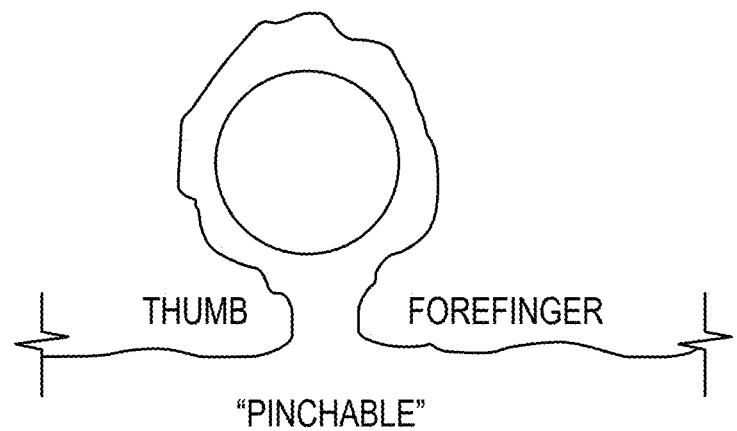
FIG. 3 illustrates the 'pinchability test'.
Figure 3:
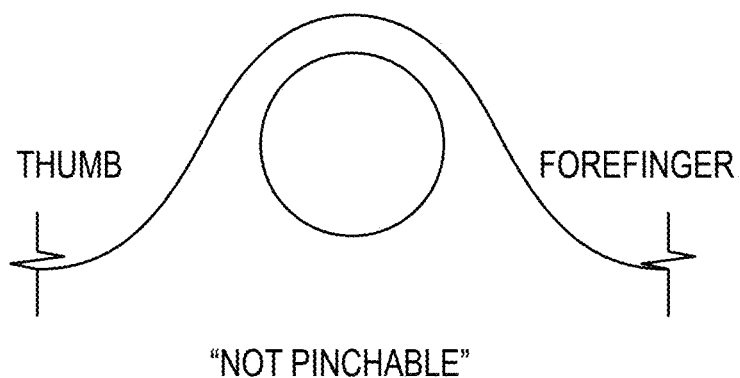

The 'pinchability test' is illustrated in FIGS. 2 and 3. As can be seen in these figures, this test goes further than the 'palpablity' test of the prior art, in that although the implant is necessarily palpable, it must also be 'pinchable'. A person should be able to isolate the implant from the underlying tissue using their thumb and forefinger and be able to move it slightly in all directions. The grip should be maintained while the implant is being moved. It should be possible for the operator to isolate the implant and maintain a grip around the implant embedded in the skin using their thumb and forefinger. For example, the 'pinchability test' would be failed if the operator was not able to maintain a grip on the implant while lifting it. This may be an indication that the implant has become embedded within the deep lying layers of tissue, or that is has been implanted too far into the skin.

In some embodiments, the 'pinchability' test is satisfied if it is possible to get the fingertips underneath the implant. This is best described by referring to FIG. 3, where the diagram on the left shows an implant that is 'pinchable' because the operator can pinch their fingertips together underneath the implant. The diagram on the right shows an implant that would fail the 'pinchability' test because it is not possible for the operator to bring their fingertips together underneath the implant, such that they feel that they can isolate the implant.

Thus, the invention provides a method for assisting an implant removal procedure on a patient, wherein the patient has a subcutaneously implanted rod and is in need of removal of said rod, comprising the steps of:

a) gripping the rod between a person's thumb and finger; and b) maintaining the grip while the person gently lifts the implant away from the underlying tissue. Being able to perform steps a) and b) represent satisfying the pinchability test described above.

Alternatively, the invention provides a method for assisting an implant removal procedure on a patient, wherein the patient has a subcutaneously implanted rod and is in need of removal of said rod, comprising the steps of:

a) gripping the rod between a person's thumb and finger; and b) not maintaining the grip while the person gently lifts the implant away from the underlying tissue. Being able to perform steps a) and b) represent not satisfying the pinchability test described above.

The selection method of the invention may also be used to determine whether a particular removal procedure is suitable for 'task-shifting', which is a term known in the art. Satisfying the 'pinchability test' may mean that the removal procedure can be performed by a healthcare practitioner of lower education and/or experience than those typically performing implant removals.). Task-shifting may also mean that the patient is deemed suitable for removal of their rod using an implant removal device (preferably as defined herein), regardless of who performs the implant removal procedure.

If a device is used in the removal procedure, the operator of the device to be used in the removal procedure should be trained in the removal procedure and should have read the instructions for use (IFU) for the device.

A device for use in the removal procedure preferably comprises:

a cutting part for cutting an opening in the skin; and a gripping part configured to move through an opening in the skin and grip the implant; such that in use, the implant is retained by the device substantially in a known position and the cutting part creates an opening in the skin through which the gripping part passes to grip the implant and remove it through the opening in the skin.

A device for use in a removal procedure of the invention preferably has an integrated scalpel such that operation of the device to the patient also effects removal of the implanted rod through the skin. It is most preferably the RemovAid™ device.

In a preferred embodiment, the implanted rod is a contraceptive implant.

In some embodiments, to be selected for the removal procedure, the skin overlying the implant must show no signs of current infection and/or is not dirty after cleaning the area and/or the patient must confirm that there is no nerve pain near the implant site and/or the implant must be intact.

In some embodiments, the removal procedure involves the use of an antiseptic and/or an anaesthetic, and to be selected for the removal procedure, the patient must confirm that they have no allergy to said antiseptic or anaesthetic.

According to certain aspects of the invention, kits are provided. These kits contain a medical device and instructions for use for the medical device.

It is required by regulatory bodies such as the Food and Drug Administration (FDA) and the European Medicines Agency (EMA) that regulated medical devices are provided with instructions for use.

As a general principle, each device must be accompanied by as much information as is necessary for an operator to use it safely, taking into account the training and knowledge of the potential users. Certain basic instructions must appear on the label with more detailed copy to be included in the enclosed instructions for use (IFU).

The IFU must contain several particulars, including the details required on the label, any side effects from use of the device, and, as a general rule, details for its correct use, including any specific precautions.

For certain medical devices such as devices that penetrate the skin, clear instructions for how to operate the device are very important, since there is potential for harm to a patient if the device is used incorrectly. In addition to instructions for using the particular device, there may be instructions for preparing the patient before using the device, such as sterilisation of the skin, or pre-selecting whether or not the device is suitable for use on a particular patient.

An aspect of the invention is a kit comprising a medical device and instructions for use for the medical device, wherein the instructions for use comprise a description of the method as described herein.

In a preferred embodiment, the medical device is an implant removal device, in particular a contraceptive rod. More preferably, the medical device is an implant removal device as described herein.

As it applies to the present invention, the instructions for use may outline the pinchability test as disclosed herein. It may be indicated that the device is only suitable for use on patients who have passed the pinchability test as described herein (for example, as described in the claims). Alternatively, it may detail additional precautions that need to be taken in regard to patients who have not passed the pinchability test.

The IFU may therefore be a critical component of the kits according to the invention. They are a technical part of the invention because following the IFU is required by regulatory bodies. The device cannot be provided or used without following the guidelines in the IFU.

EXAMPLES

The results of the following clinical study (REVALID02) illustrates the invention.

The study was a prospective, single-centre, non-comparative feasibility investigation to evaluate performance and safety of RemovAid™ Retrieval Device (class IIa) when used for removal of palpable subdermal contraceptive rod implants was conducted.

The primary objective was to evaluate the performance of the IMD when used for removal of palpable subdermal Implanon®/Nexplanon® contraceptive implants (Cis).

Primary Endpoint
Percentage of fixated implants that were successfully removed without the use of additional tools.
Secondary Endpoints
Frequency, severity, causality and outcome of Adverse Events (AEs) (including anticipated Adverse Device Effects [ADEs]) and device deficiencies.
Mean pain score (maximum pain intensity during the procedure) indicated by the subject on a Visual Analogue Scale (VAS) 0-100 mm ruler, assuming that anaesthesia had been properly administered.
Percentage of palpable implants where the implant could be seen and/or felt on both sides of the clamp after a reasonable number of attempts of fixation, as judged by the Investigator.
Mean time from;
a) making incision until implant was removed.
b) first touching the patient with the device until the implant was removed.
Intra -and inter operator variability of duration of the procedure (from making incision until implant was removed and from first touching the patient with the device until the implant was removed).
Fulfillment of pre-defined technical requirements, as documented on an operator functionality questionnaire.
The operator's global impression of the IMD was assessed using a 5-point scale.
Number of Subjects
Planned
The intention was to include 25 subjects in order to get 20 subjects with a complete procedure (i.e. successful fixation), assuming a 20% failure to fixate rate.
Screened, Included and Completed

| Description | Number of subjects |
|---|---|
| Screened | 19 |
| Included | 19 |
| Completed (successful fixation) | 17 |
| Withdrawn (Fixation failure) | 2 |
| Included in The Full Analysis Set (FAS) | 19 |
| Included in FAS-fixation population | 17 |
| Implant successfully removed with the IMD | 12 |
| Implant not removed with the IMD | 5 |

Diagnosis and Main Eligibility Criteria

Female subjects, age 18 years and above, presenting to a recruitment clinic for removal of a palpable subdermal Implanon®/Nexplanon® CI were considered for participation.

Methodology

Subjects with palpable subdermal CIs were recruited from advertising and by referrals from a network of youth guidance centres. The subjects contacted the investigational site for scheduling a first appointment (Visit 1). Brief oral information about the investigation was given by phone. The formal enrollment and signing of the Informed Consent Form (ICF) took place at the Investigational site at Visit 1, before any investigation-specific procedures were performed.

Consenting subjects were screened for eligibility according to pre-defined inclusion/exclusion criteria (see below). For eligible subjects, the removal procedure was performed on the same day.

There was only exposure to one IMD per subject. Any removal procedure in which the device did not successfully fixate the CI after a reasonable number of attempts resulted in abortion of the investigational procedure without attempted incision or extraction by means of the device. The CI removal was subsequently performed according to the current standard of care.

In order to assess the inter- and intra-operator procedural variability, the removal procedure was performed by four different operators performing 3-7 procedures each. The removal procedure was video recorded for documentation of the IMD performance.

A follow-up visit for inspection of the removal site and reporting and follow-up of any AEs was performed seven days (±1 day) following the procedure. The removal site was inspected and subjects were asked about any AE occurred since the procedure. If a visit to the research site was not possible, a telephone interview or e-mail contact could be performed and the subject was asked to send a photo of the removal site as a Multimedia Messaging Service (MMS).

Investigational Medical Device, Dosage and Mode of Administration

The RemovAid™ Retrieval Device is a single use surgically invasive device intended for removal of palpable subdermal Implanon®/Nexplanon® CIs, which are small hormone-releasing plastic rods inserted under the skin, typically in the upper arm. RemovAid™ is intended to simplify and standardise the removal procedure to match the level of complexity to that of implant insertion and to reduce inter- and intra-operator procedural variability for implant removal.

Results

Of all successfully fixated implants, 70.6% were successfully removed using the IMD as intended. Eighty-nine percent of all implants were successfully fixated by the IMD.

The mean duration of the entire procedure from first touching the subject with the device until implant extraction was 2 min 30 sec, and the mean duration from incision until extraction was 1 min 19 sec.

The slowest operator mean removal time (3 min 12 sec) was 1 min 34 sec slower than the fastest operator mean time (1 min 9 sec) for the entire procedure. From incision to extraction, the difference between the slowest (2 min 1 sec) and fastest (0 min 53 sec) was 1 min 8 sec.

In the remaining three removal failures, the failure of the Pincher to retain the implant during extraction appeared to be the cause of failure.

For several (2-4) of the device removal failures, the Pincher was hard to move down, which may have contributed to the failure to successfully remove the implants. This was detected for an additional 19 devices during a pre-use functionality test.

For the successful removals, the average global impression of the IMD by the operators was 4.3 on a scale from 1-5. Subjects undergoing a successful device removal scored the procedure on average 4.8 on a scale from 1-5.

General Description and Intended Use

The RemovAid™ Retrieval Device is a Class IIa (rule 6) single use surgically invasive device intended for removal of palpable subdermal Implanon®/Nexplanon® CIs, which are small hormone-releasing plastic rods with a diameter of 2.0 mm inserted under the skin, typically in the upper arm.

The device fixates the CI whilst implanted under the skin, incises the skin and the fibrous sheath covering the implant, followed by mechanical extraction of the implant.

The intended user shall be a health care provider with sufficient training, skills and authorization to remove one-rod CIs. The intended user should possess the skills necessary to successfully operate the RemovAid™, and to understand the functions and operating parameters of the RemovAid™

Figure 1:
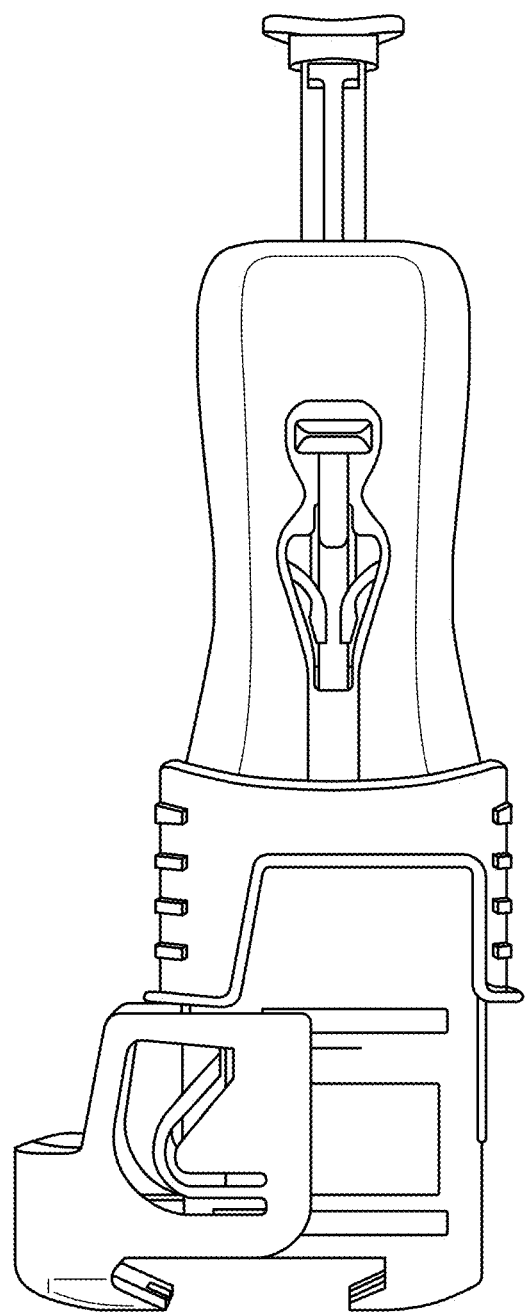
FIG. 1 shows the RemovAid™ device that may be used in a method according to the invention.

An overview picture of the IMD is given in FIG. 1

A medical history was taken prior to removal. Implant characteristics were recorded as part of the medical history. Descriptive statistics are presented in the table shown below:

| Descriptive statistics; Implant characteristics | | | | | | |
|---|---|---|---|---|---|---|
| | | FAS (N = 19) | Fixation Failure (N = 2) | FAS-fixation (N = 17) | IMD-success (N = 12) | IMD-Failure (N = 5) |
| Months since implant insertion | n/nmiss | 19/0 | 2/0 | 17/0 | 12/0 | 5/0 |
| | Mean (SD) | 30.5 (17.0) | 5.5 (0.7) | 33.5 (15.4) | 32.8 (16.2) | 35.2 (14.7) |
| | Median (Min, Max) | 30 (5.0, 60.0) | 5.5 (5.0, 6.0) | 31.0 (6.0, 60.0) | 33.0 (6.0, 60.0) | 31.0 (24.0, 60.0) |
| Implant visible under skin? | n/nmiss | 19/0 | 2/0 | 17/0 | 12/0 | 5/0 |
| | Number (%) | 6 (31.6%) | 0 (0.0%) | 6 (35.3%) | 5 (41.7%) | 1 (20.0%) |
| Completely and easily palpable? | n/nmiss | 19/0 | 2/0 | 17/0 | 12/0 | 5/0 |
| | Number (%) | 16 (84.2%) | 0 (0.0%) | 16 (94.1%) | 12 (100.0%) | 4 (80.0%) |
| Implant "pinchable"? | n/nmiss | 19/0 | 2/0 | 17/0 | 12/0 | 5/0 |
| | Number (%) | 18 (94.7%) | 1 (50.0%) | 17 (100.0%) | 12 (100.0%) | 5 (100.0%) |
| Subjective depth assessment (0-4) | n/nmiss | 19/0 | 2/0 | 17/0 | 12/0 | 5/0 |
| | Mean (SD) | 3.1 (0.9) | 1.0 (0.0) | 3.4 (0.6) | 3.5 (0.5) | 3.0 (0.7) |
| | Median (Min, Max) | 3.0 (1.0, 4.0) | 1.0 (1.0, 1.0) | 3.0 (2.0, 4.0) | 3.5 (3.0, 4.0) | 3.0 (2.0, 4.0) |

The five devices that successfully fixated the implant but failed to successfully remove the implant were interpreted as device deficiencies and reviewed for apparent cause of removal failure. Additionally, any device deficiency/malfunction listed on the product accountability log was added to the deficiency analysis.

In two of the failed removals, the implant was cut so deep that it was broken into two pieces during extraction. Most likely, this was due to the incision being too deep, another contributing factor may have been that too much tissue was grasped by the clamp.

The mean time since implant insertion was 30.5 (SD 17.0) months for the FAS population. The mean was lower (5.5 [SD 0.7] months) for the fixation failure population, and slightly higher for all other groups.

Six of the implants (31.6% of FAS) had visible contours under the skin prior to removal. All of these were in the FAS fixation population; five in the IMD success and one in the IMD failure population, respectively. None of the fixation failure implants had visible contours under the skin.

Sixteen of the implants (84.2% of FAS) were reported as being completely and easily palpable. The three implants reported as not easily and/or completely palpable were in the IMD failure population (n=1), and in the fixation failure population (n=2, reported as "easily palpable at the ends" and "can hardly palpate one side of the rod").

All except one implant (94.7%) in the FAS population were reported as "pinchable", possible to grasp and maintain hold of the implant under the skin using opposing thumb and forefinger. The one non-pinchable implant was in the fixation failure population.

The operator indicated the subjective depth of the implant in the subject arm within a range of 0-4. (0=very deep, 1=deep, 2=superficial, 3=very superficial, 4=visible). The mean implant depth was 3.1 (SD 0.9) in the FAS population. The mean was lower in the fixation failure population (1.0 [SD 0.0]) and the IMD-failure population (3.0 [SD 0.7]) while it was slightly higher in the FAS-Fixation and the IMD-success populations (mean 3.4 [SD 0.6] and 3.5 [SD 0.5], respectively).

In conclusion, ensuring that the implant is palpable and 'pinchable' increases the likelihood of a successful removal and should be considered as a pre-requisite for attempting removal of an implant using an implant removal device.

The invention claimed is:

1. A method for selecting a patient for an implant removal procedure, wherein the patient has a subcutaneously implanted rod and is in need of removal of said rod, wherein the patient is selected as being suitable for the removal procedure if the rod can be gripped between a person's thumb and finger and the grip can be maintained while the person gently lifts the implant away from the underlying tissue, and wherein the patient is selected as suitable for the removal procedure responsive to at least one of the person's thumb and finger being maintained between the implant and the underlying tissue concurrently with the implant being lifted away from the underlying tissue.

2. A method according to claim 1, wherein the implant removal procedure comprises the use of an implant removal device.

3. A method according to claim 2, wherein the implant removal device fixes and retains the position of the rod relative to the overlying skin, such that the rod can be located and removed by an operator of the device.

4. A method according to claim 2, wherein the device has an integrated scalpel such that operation of the device facilitates both fixing and retaining the position of the implant and removal of said implant through the skin.

5. A method according to claim 2, wherein the device comprises:
   a cutting part for cutting an opening in the skin; and
   a gripping part configured to move through an opening in the skin and grip the implant; such that in use, the implant is retained by the device substantially in a known position and the cutting part creates an opening in the skin through which the gripping part passes to grip the implant and remove it through the opening in the skin.

6. A method according to claim 1, wherein once the operator has gripped the rod, it can be moved slightly in all directions.

7. A method according to claim 1, wherein the implanted rod is a contraceptive implant.

8. A method according to claim 1, wherein to be selected for the removal procedure, the skin overlying the implant must show no signs of current infection and/or is not dirty after cleaning the area.

9. A method according to claim 1, wherein to be selected for the removal procedure, the patient must confirm that there is no nerve pain near the implant site.

10. A method according to claim 1, wherein to be selected for the removal procedure, the implant must be intact.

11. A method according to claim 1, wherein the removal procedure involves the use of an antiseptic and/or an anaesthetic, and to be selected for the removal procedure, the patient must confirm that they have no allergy to said antiseptic or anaesthetic.

12. A method for removing a subcutaneously implanted rod from a patient in a removal procedure that comprises making an incision in the patient's skin and locating and removing the implanted rod through the opening in the skin, wherein the patient is selected for the removal procedure using the method of claim 1.

13. A method according to claim 12, wherein the removal procedure comprises the use of an implant removal device, optionally wherein the implant removal device has an integrated scalpel such that operation of the device effects both the incision and the removal.

14. A method according to claim 13, wherein the device comprises:
   a cutting part for cutting an opening in the skin; and
   a gripping part configured to move through an opening in the skin and grip the implant; such that in use, the implant is retained by the device substantially in a known position and the cutting part creates an opening in the skin through which the gripping part passes to grip the implant and remove it through the opening in the skin.

15. A kit comprising a medical device and instructions for use for the medical device, wherein the instructions for use comprise a description of the method according to claim 1.

16. A kit according to claim 15, wherein the medical device is an implant removal device, in particular a contraceptive rod.

17. A kit according to claim 15, wherein the medical device is an implant removal device as described in claim 5.

* * * * *